United States Patent
Kachelries et al.

(10) Patent No.: US 6,563,309 B2
(45) Date of Patent: May 13, 2003

(54) USE OF EDDY CURRENT TO NON-DESTRUCTIVELY MEASURE CRACK DEPTH

(75) Inventors: James S. Kachelries, Wallingford, PA (US); Louis R. Truckley, Oxford, PA (US); Douglas P. Knapp, Devon, PA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 09/965,752

(22) Filed: Sep. 28, 2001

(65) Prior Publication Data

US 2003/0062892 A1 Apr. 3, 2003

(51) Int. Cl.$^7$ .................. G01N 27/90; G01N 27/82; G01R 35/00
(52) U.S. Cl. .................. 324/238; 324/240; 324/202; 324/225; 702/38
(58) Field of Search .............. 324/220–228, 324/238, 240, 241, 242, 202; 702/38, 85; 364/507.01

(56) References Cited

U.S. PATENT DOCUMENTS

| | | | | |
|---|---|---|---|---|
| 4,088,953 A | * | 5/1978 | Sarian | 324/232 |
| 4,628,261 A | * | 12/1986 | Huschelrath et al. | 324/227 |
| 4,906,927 A | * | 3/1990 | Urata et al. | 324/233 |
| 4,963,826 A | * | 10/1990 | Capobianco et al. | 324/202 |
| 5,365,169 A | * | 11/1994 | Hosohara et al. | 324/220 |
| 5,559,431 A | * | 9/1996 | Sellen | 324/202 |
| 6,424,151 B2 | * | 7/2002 | Kawata et al. | 324/220 |

FOREIGN PATENT DOCUMENTS

JP 404120458 A1 * 4/1992 .......... G01N/27/83

* cited by examiner

Primary Examiner—Edward Lefkowitz
Assistant Examiner—Darrell Kinder
(74) Attorney, Agent, or Firm—Harness Dickey & Pierce P.L.C.

(57) ABSTRACT

A method and apparatus for non-destructively measuring the depth of a crack with precision and accuracy in a workpiece using an eddy current process. The method involves empirically creating a response curve of the eddy current response produced from crack(s) in a sample workpiece(s), wherein the depth of the crack(s) in the sample workpiece(s) may be modified a plurality of times and an eddy current response reading is taken at each different crack depth. The response curve is then used to interpolate the depth of a crack in a workpiece composed of the same material non-destructively by measuring the eddy current response in the workpiece crack and then obtaining the predetermined crack depth value form the response curve.

8 Claims, 5 Drawing Sheets

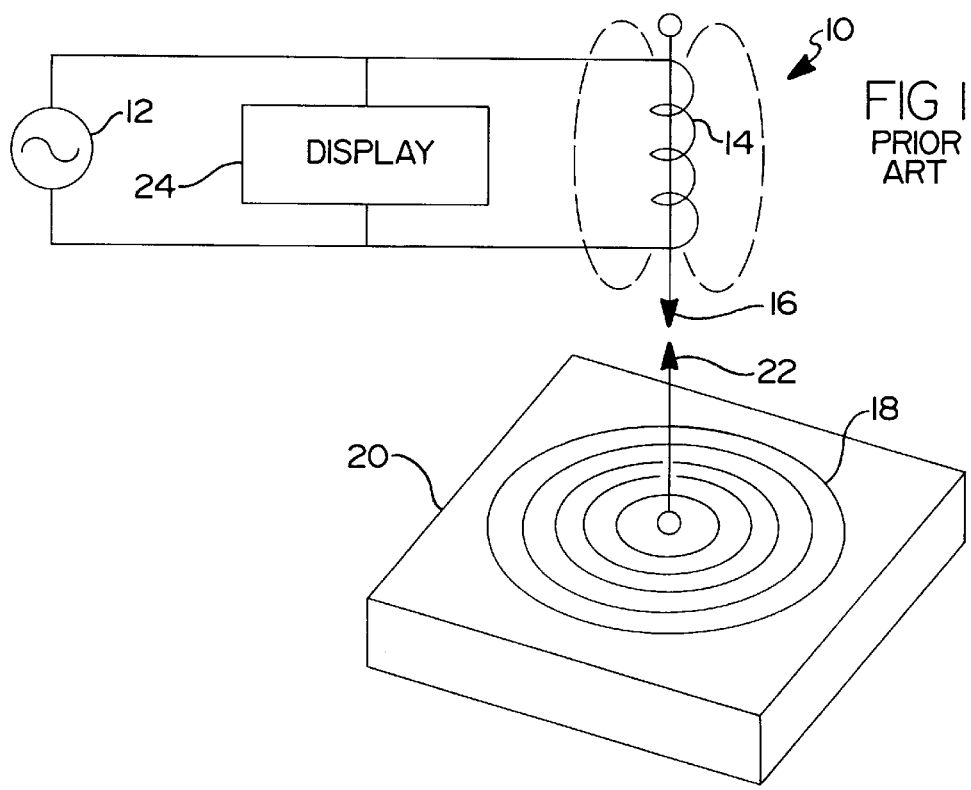
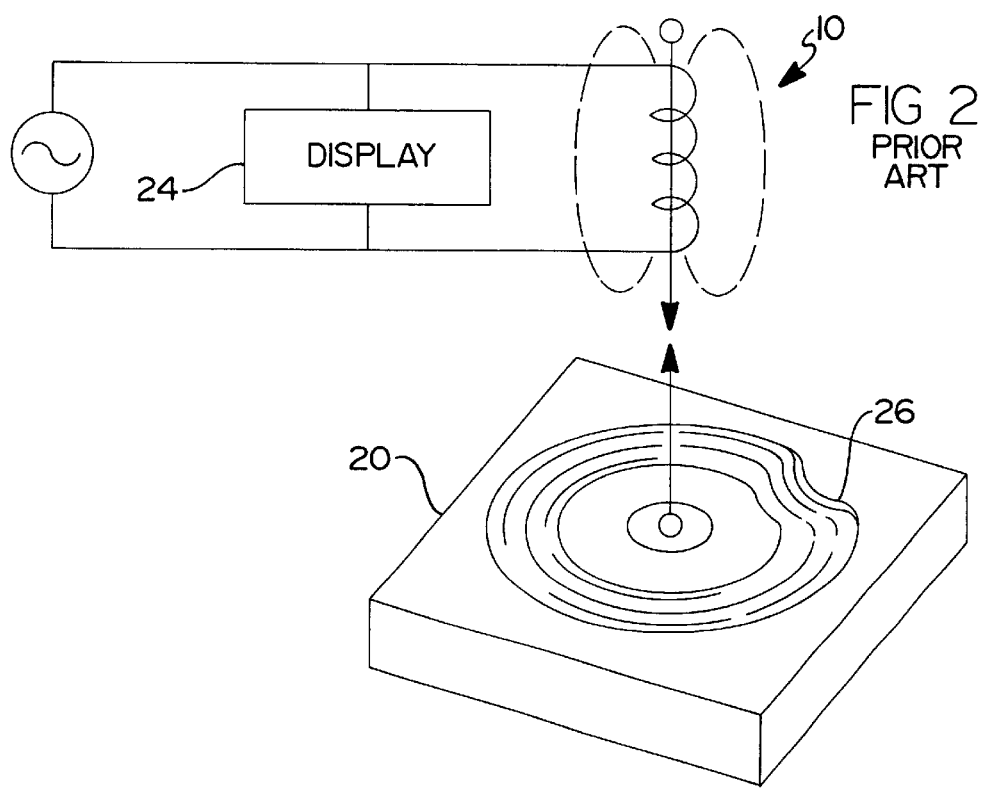

EDDY CURRENT RESPONSE 100
TOTAL THICKNESS 0.040

EDDY CURRENT RESPONSE 70
TOTAL THICKNESS 0.035

EDDY CURRENT RESPONSE 50
TOTAL THICKNESS 0.030

EDDY CURRENT RESPONSE 15
TOTAL THICKNESS 0.025
OPEN CRACK-DEPTH=0.005

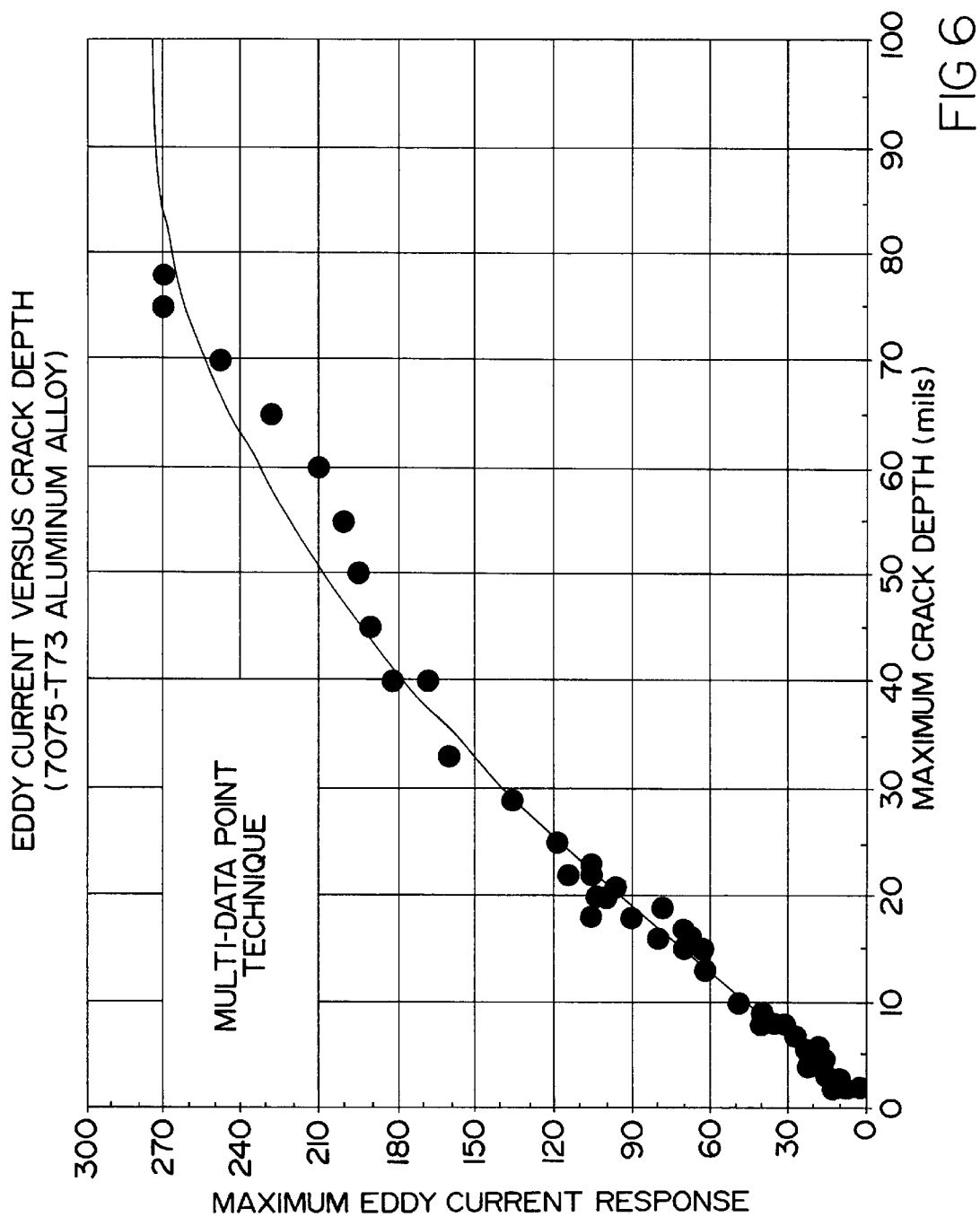

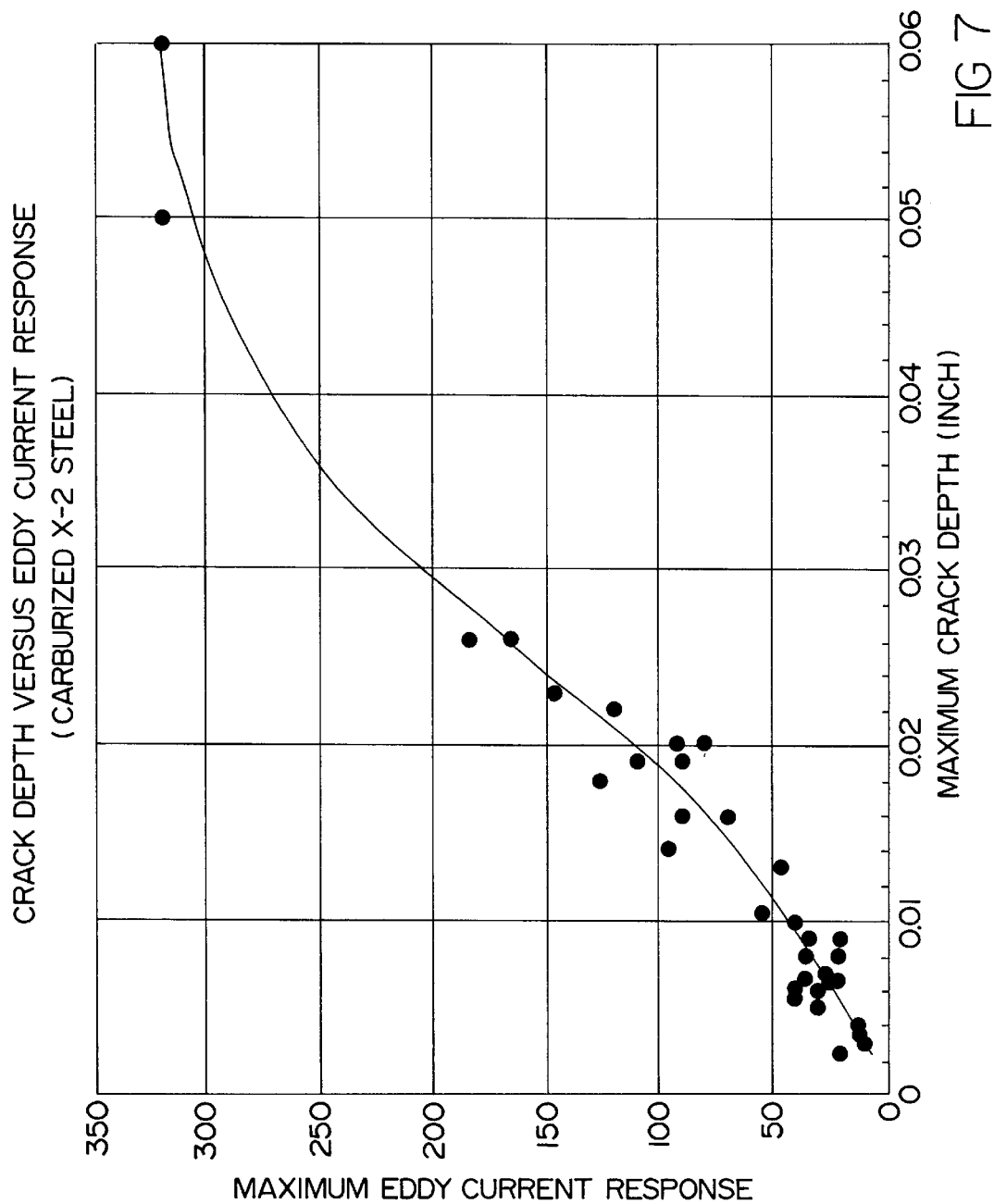

USE OF EDDY CURRENT TO NON-DESTRUCTIVELY MEASURE CRACK DEPTH

FIELD OF THE INVENTION

The present invention relates particularly to a method and apparatus for measuring (quantifying) the depths of cracks in workpieces through the use of eddy currents measured in workpieces.

BACKGROUND OF THE INVENTION

The use of eddy current testing technology to detect and locate anomalies in materials is well established. Eddy current testing is the process of inducing small electrical currents by a device into an electrically conductive workpiece and observing the resultant reaction between the magnetic fields involved. Cracks in conductive materials affect the flow of these eddy currents that can be detected and related to the depth of a crack.

By way of further background, eddy currents are created in a workpiece when alternating current flows in a coil in close proximity to a conducting surface of the workpiece. The magnetic field of the coil will induce circulating eddy currents in that surface. The magnitude and phase of the eddy currents will affect the loading on the coil and thus its impedance. When a flaw is detected in the surface of the material, the eddy current flow will be interrupted or reduced, thus decreasing the loading on the coil and increasing its effective impedance.

Though conventional eddy current technology is capable of detecting cracks and/or flaws in conductive material, it has not been used to measure the depth of a crack in a non-destructive manner. The traditional method used to measure crack depth is to mechanically open the crack or cross-sectioning through the crack. This approach is destructive because of the damage done to the workpiece in determining the crack depth. Therefore, it is ineffective, time consuming and costly. A need exists for a technique whereby the depth of a crack can be measured accurately without destroying the workpiece.

SUMMARY OF THE INVENTION

The present invention overcomes the above-described drawbacks through an apparatus and method that non-destructively measures surface crack depths on components with precision and accuracy using an eddy current testing process. This non-destructive process is beneficial whereby eliminating the need to destructively cross-section through the crack. In addition, machining an amount of material as determined by this invention might repair components exhibiting crack indications. This method utilizes established eddy current instruments and a known (i.e., previously empirically determined) relationship between eddy current response and crack depth. The crack is initially detected and located by proven non-destructive methods such as but not limited to magnetic particle inspection, fluorescent penetrant inspection, eddy current testing, and/or visual or microscopic examination. The eddy current response, which by way of example may be a real-time display of the probe impedance in the form of, again by way of example, a refreshing dot on a display screen, indicates a change in impedance, visually manifested by way of example as a vertical rise and drop, or trace, of the aforementioned dot, as a probe of a measuring instrument passes over the surface to be evaluated. When a crack is not present and the material is absent of other anomalies affecting eddy currents, the impedance is constant and there is effectively no change in the signal, or no eddy current response, manifested by way of example as a stationary or tightly-tracing dot in the aforementioned example of response display. However, if there is a crack (or other anomaly that affects eddy currents) then the impedance changes. Crack responses result in mostly vertical signal changes when the measuring device is so altered. The magnitude of a signal change due to a crack, referred to henceforth as "response", is proportional to the depth of the crack.

The relationship between the eddy current response and crack depth is determined empirically by generating a table of data points with each point defined by two parameters: 1) maximum eddy current signal response measured from the crack, and 2) actual depth of said crack from 1) measured with the proven method of mechanical opening. Each data point represents a unique crack and the accumulation of many data points defines a curve representing the relationship between eddy current response and crack depth. The curve is relevant to a specific material. The curve is then applied as a tool to predict the crack depth in a component of the same material from the measured eddy current response in a non-destructive manner. The term unique, as in reference to a crack, as used herein may by way of example refer to 1) cracks in, the same workpiece separated by a distance or, 2) to cracks in different workpieces of the same material or, 3) to several cracks originating from (that is, at one time having been part of) a single original crack where the original crack having surface material removed (thereby effectively decreasing its depth) effectively becomes another crack, shallower and unique to the original (deeper) crack, from the perspective of eddy current response.

BRIEF DESCRIPTION OF THE DRAWINGS

The present invention will become more fully understood from the detailed description and the accompanying drawings, wherein:

FIG. 1 shows an eddy current instrument for generating an eddy current flow in an unflawed, electrically conductive material;

FIG. 2 shows an eddy current instrument generating an eddy current flow in a flawed or cracked electrically conductive material;

FIG. 6 is a graph depicting the eddy current response versus crack depth in electrically conductive 7075-T73 aluminum alloy material; and FIG. 7 is a graph depicting the eddy current response versus crack depth in electrically conductive carburized X-2 steel.

DETAILED DESCRIPTION OF THE PREFERRED EMBODIMENTS

Figure 3A:
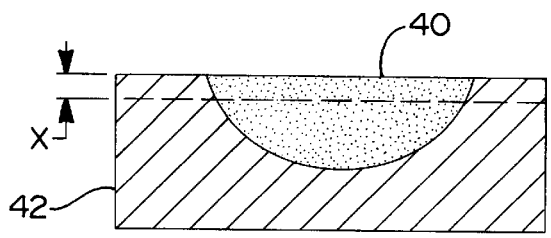
FIGS. 3a–3d show views of "unique" cracks emanating from a single original crack in a specimen of conductive material, wherein successive surface layers have been removed from the specimen during the process of empirically determining crack depth, and the term "unique" is used as described previously herein to illustrate the method (called "multi-data-point technique") of generating many data points from a single original crack.

The following description of the preferred embodiments is merely exemplary in nature and is in no way intended to limit the invention, its application, or uses.

With reference to FIGS. 1 and 2, wherein like numbers designate like components throughout all the figures, an eddy current system 10 includes an alternating current source 12 electrically connected to a test coil 14. The test coil 14 produces a magnetic field 16 and induces eddy currents 18 in a workpiece or material 20. The eddy currents produce an opposing magnetic field 22, which is coupled back to the test coil 14. A display 24 of the system 10 displays the eddy current response in terms of impedance. When no crack is present, the impedance is unchanged and there is no response detected by the system 10.

Specifically, FIG. 2 shows the workpiece 20 having the presence of a material fault (i.e., crack). A change in the eddy current flow 26 results from this crack and this discontinuity can be observed as a change in coil impedance, as the display 24 indicates.

In order to establish a precise relationship between eddy current response and crack depth, a plot of eddy current response versus crack depth must be generated empirically whereby each data point represents a specific eddy current response for a specific depth crack, in the specific material. FIGS. 3a–3d show views of a single piece of material 42 having a crack 40.

Figure 3B:
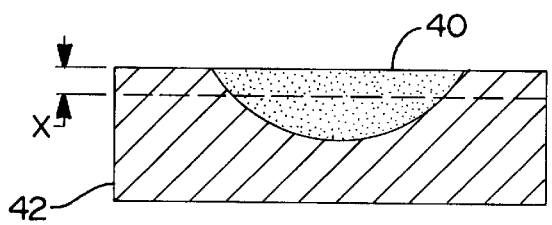
Figure 3C:
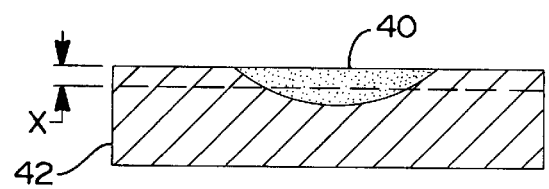
Figure 3D:
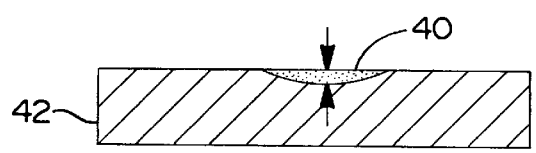

Beginning with FIG. 3a, an initial eddy current response is measured for the original crack 40 in material 42. The next step is to remove a predetermined layer of conductive material, represented by "X", where X in this example is equal to 0.005 inch. Provided the amount, or depth, of removed material is known, removal steps can have unequal layers. The resulting sample material is shown in FIG. 3b. When this layer of material is removed, the crack 40 is shallower, and unique from the original crack in FIG. 3a, and the eddy current response is again measured and recorded. Another layer of material having the thickness X is then removed from the sample material 42, thus reducing its thickness further, as indicated in FIG. 3c. The eddy current response is then measured again and recorded. Another layer X of material is then removed from the sample material 42 to leave the sample material with a thickness as shown in FIG. 3d. This process is repeated, as shown in FIGS. 3b–3d, until the eddy current response produced by the material 42 approaches being unappreciable. The crack 40 in the sample material 42 of FIG. 3d now still has a depth suitable to be mechanically opened and measured using well known optical methods to precisely determine the actual depth of the crack 40.

Figure 4:
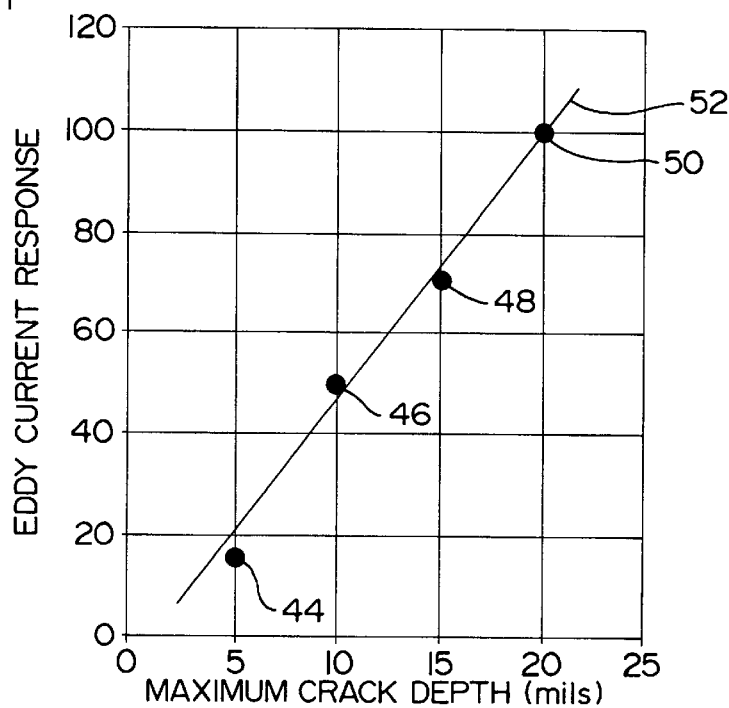
FIG. 4 is a graph depicting the eddy current response versus the maximum crack depth generated by the process of empirically measuring crack depth in connection with FIGS. 3a–3d.

Working backwards from FIGS. 3d–3a, the actual crack depth for each previous eddy current response measurement can be calculated. This is done by adding the amount of removed material (0.005 inch) to the known depth of the opened crack in FIG. 3d. Thus, the measured eddy current response of the sample material 42 in FIG. 3d is plotted on a graph. This appears as point 44 in FIG. 4. The amount of removed material is then added to this crack depth to calculate the crack depth corresponding to the sample material 42 as shown in FIG. 3c. This crack depth and its previously measured eddy current response define a data point that is plotted on the graph of FIG. 4 as point 46.

Another 0.005 inch (removed material) is then added to the crack depth determined in connection with the sample material 42 of FIG. 3c to determine the actual crack depth of crack 40, as shown in the sample material 42 of FIG. 3b. This determined crack depth and its corresponding eddy current response define another data point that is plotted on the graph of FIG. 4 as point 48.

Finally, another 0.005 (removed material) inch is added to the determined crack depth of the crack of the sample material 42 of FIG. 3b to determine the actual depth of the crack 40 shown in FIG. 3a. This determined crack depth and the previously recorded eddy current response for the sample material 42 shown in FIG. 3a define another data point that is then plotted as point 50 in the graph of FIG. 4. The resulting collection of plotted points 44–50 define a response curve 52 which can be used to interpolate the depth of a crack in a workpiece of the same type of material simply by obtaining a non-destructively-measured eddy current response of the crack.

Figure 5:
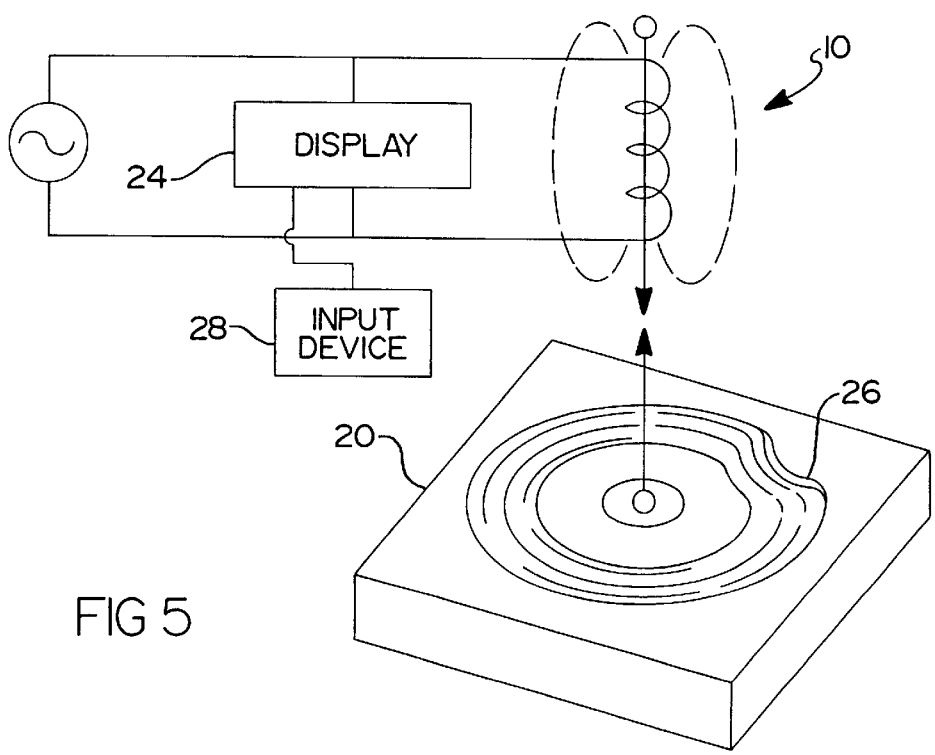
FIG. 5 shows an eddy current instrument attached to separate or integrated components generating an eddy current flow in a flawed or cracked electrically conductive material.

In practice, the response curve 52 may be employed in the form of an apparatus comprised of a look-up table used in connection with the eddy current measuring instrument. We envision having response curves for various specific materials stored in computer memory. Using a device like a keyboard to input the specific material being evaluated to determine crack(s) depth, running the measuring probe over the crack will display the crack depth at the given measurement location. Separate or integrated components (such as an input device) represented by item 28 in FIG. 5 could be used to perform the functions of measuring, storing response curves and measurement data points, and displaying real-time measurement responses in the form(s) of a moving dot and/or numerical crack depth based on interpolation from the said selected response curves. The measurement device could utilize different models of eddy current testing machines that have alterable signal parameters. The instrument used to generate the data presented herein was the ZETEK MIZ-21A Eddy Current Instrument.

Additionally, eddy current response versus crack depth curves can be generated for different types of materials. FIGS. 6 and 7 illustrate multiple data points generated from cracks in 7075-T73 aluminum alloy and carburized X-2 steel, respectively. Once the data points have been measured and plotted, a response curve accurately establishing the crack depth for each type of material can be created.

An important advantage of the present invention is that crack depth can be determined non-destructively. Thus, this invention allows the depth of a crack to be determined without affecting the integrity of the workpiece being evaluated.

The description of the invention is merely exemplary in nature and, thus, variations that do not depart from the gist of the invention are intended to be within the scope of the invention. Such variations are not to be regarded as a departure from the spirit and scope of this invention.

What is claimed is:

1. A method for using eddy currents to non-destructively measure the depth of a crack in a workpiece, the method comprising:
   a) electrically exciting a sample workpiece having a crack of an initially unknown depth a plurality of times as a depth of said crack is altered by removing successive layers of said sample workpiece;
   b) recording measured eddy current responses generated by said sample workpiece as a result of electrically exciting said sample workpiece in step a);
   c) using information obtained in steps a) and b) to produce a response curve indicative of an eddy current response that results at each one of a plurality of different crack depths;

d) electrically exciting an actual workpiece having a crack of initially unknown depth, said actual workpiece comprised of the same material as said sample workpiece;

e) recording a measured eddy current response generated by said actual workpiece as a result of electrically exciting said actual workpiece; and f) comparing the measured eddy current response of said actual workpiece to said response curve and interpolating from said response curve the depth of said crack of said actual workpiece.

2. The method of claim 1, wherein step a) comprises removing successive layers having a known thickness from said sample workpiece.

3. The method of claim 1, wherein step a) further comprises measuring crack depth by mechanically opening said crack.

4. The method of claim 1, wherein said sample workpiece and said actual workpiece are fabricated from 7075-T73 aluminum alloy.

5. The method of claim 1, wherein said sample workpiece and said actual workpiece are fabricated from carburized X-2 steel.

6. A method for creating a response curve for use in determining the depth of a crack in a material, the method comprising the steps of:

recording a measured eddy current response from a material having a crack of a known depth;

removing a layer of said material;

recording a new measured eddy current response on said material with said crack having a new known depth;

repeating the steps of removing a layer and recording a response until the difference between eddy current responses becomes approximately zero; and creating a response curve from said recorded measurements of eddy current responses.

7. The method of creating a response curve of claim 6, wherein the step of removing a layer of said material includes removing a layer having a known depth from said material.

8. The method of creating a response curve of claim 6, wherein the step of creating said response curve includes plotting measured eddy current responses in relation to measured crack depths for each one of said measured eddy current responses, thereby producing a response curve from which the depth of a crack in a component made from the same material can be interpolated.

* * * * *